United States Patent
Yano et al.

(10) Patent No.: US 9,066,929 B2
(45) Date of Patent: Jun. 30, 2015

(54) THERAPEUTIC METHOD FOR MESOTHELIOMA

(71) Applicants: NATIONAL UNIVERSITY CORPORATION KANAZAWA UNIVERSITY, Kanazawa-shi, Ishikawa (JP); KYOWA HAKKO KIRIN CO., LTD., Tokyo (JP)

(72) Inventors: Seiji Yano, Ishikawa (JP); Yusuke Machino, Tokyo (JP); Yui Suzuki, Tokyo (JP)

(73) Assignees: NATIONAL UNIVERSITY CORPORATION KANAZAWA UNIVERSITY, Kanazawa-shi (JP); KYOWA HAKKO KIRIN CO., LTD., Tokyo (JP)

( * ) Notice: Subject to any disclaimer, the term of this patent is extended or adjusted under 35 U.S.C. 154(b) by 0 days.

(21) Appl. No.: 14/097,294

(22) Filed: Dec. 5, 2013

(65) Prior Publication Data

US 2014/0220003 A1  Aug. 7, 2014

Related U.S. Application Data

(60) Provisional application No. 61/734,087, filed on Dec. 6, 2012.

(51) Int. Cl.

| | | |
|---|---|---|
| A61K 39/395 | (2006.01) | |
| G01N 33/574 | (2006.01) | |
| A61K 45/06 | (2006.01) | |
| C07K 16/18 | (2006.01) | |

(52) U.S. Cl.
CPC ............ *A61K 39/3955* (2013.01); *A61K 39/395* (2013.01); *G01N 33/57423* (2013.01); *A61K 45/06* (2013.01); *C07K 16/18* (2013.01); *G01N 2405/10* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 5,830,470 | A | 11/1998 | Nakamura et al. |
| 5,874,255 | A | 2/1999 | Nakamura et al. |
| 5,939,532 | A | 8/1999 | Nakamura et al. |
| 6,042,828 | A * | 3/2000 | Nakamura et al. ......... 424/133.1 |
| 6,423,511 | B1 | 7/2002 | Nakamura et al. |
| 6,872,392 | B2 | 3/2005 | Nakamura et al. |
| 7,781,569 | B2 * | 8/2010 | Fanger et al. ............. 530/387.3 |
| 2006/0210555 | A1 | 9/2006 | Kensil |
| 2007/0134242 | A1 | 6/2007 | Nishimoto et al. |
| 2007/0172476 | A1 | 7/2007 | Ueda et al. |
| 2009/0028877 | A1 | 1/2009 | Iida et al. |
| 2010/0111947 | A1 | 5/2010 | Ishii et al. |
| 2011/0236374 | A1 | 9/2011 | Shitara et al. |

FOREIGN PATENT DOCUMENTS

| | | |
|---|---|---|
| EP | 0 882 794 A2 | 12/1998 |
| JP | 10-257893 A | 9/1998 |
| JP | 2005-532257 A | 10/2005 |
| WO | 03/049704 A2 | 6/2003 |
| WO | 2004/053102 A2 | 6/2004 |
| WO | 2007/013627 A1 | 2/2007 |
| WO | 2010/018846 A1 | 2/2010 |

OTHER PUBLICATIONS

Kayser et al., "Glyco- and Immunohistochemical Refinement of the Differential Diagnosis between Mesothelioma and Metastatic Carcinoma and Survival Analysis of Patients", Journal of Pathology, 2001, vol. 193, pp. 175-180.

Li et al., "The Therapeutic Efficacy of Anti-Vascular Endothelial Growth Factor Antibody, Bevacizumab, and Pemetrexed against Orthotopically Implanted Human Pleural Mesothelioma Cells in Severe Combined Immunodeficient Mice", Clinical Cancer Research, Oct. 1, 2007, vol. 13, No. 19, pp. 5918-5925.

Li et al., "Pleural Mesothelioma Instigates Tumor-Associated Fibroblasts to Promote Progression via a Malignant Cytokine Network", The American Journal of Pathology, Sep. 2011, vol. 179, No. 3, pp. 1483-1493.

Nakamura, et al., "Dissection and Optimization of Immune Effector Functions of Humanized Anti-Ganglioside GM2 Monoclonal Antibody", Molecular Immunology, 2000, vol. 37, pp. 1035-1046.

Syrokou et al., "Proteoglycans in Human Malignant Mesothelioma. Stimulation of their Synthesis Induced by Epidermal, Insulin and Platelet-Derived Growth Factors Involves Receptors with Tyrosine Kinase Activity", Biochimie, 1999, vol. 81, pp. 733-744.

Tanaka et al., "A Novel Monoclonal Antibody Against Murine IL-2 Receptor β-Chain Characterization of Receptor Expression in Normal Lymphoid Cells and EL-4 Cells", The Journal of Immunology, Oct. 1, 1991, vol. 147, No. 7, pp. 2222-2228.

Yano et al., "Antiangiogenic Therapies for Malignant Pleural Mesothelioma", Frontiers in Bioscience, Jan. 1, 2011, vol. 16, pp. 740-748.

Hanibuchi et al., "Immunological Circumvention of Multiple Organ Metastases of Multidrug Resistant Human Small Cell Lung Cancer Cells by Mouse-Human Chimeric Anti-Ganglioside GM2 Antibody KM966", Clinical & Experimental Metastasis, 2001, vol. 18, pp. 353-360.

Zebrowski et al., "Vascular Endothelial Growth Factor Levels and Induction of Permeability in Malignant Pleural Effusions", Clinical Cancer Research, Nov. 1999, vol. 5, pp. 3364-3368.

Broaddus, "Asbestos, the Mesothelial Cell and Malignancy: A Matter of Life or Death", American Journal of Respiratory Cell and Molecular Biology, 1997, vol. 17, pp. 657-659.

(Continued)

*Primary Examiner* — Sheela J Huff
(74) *Attorney, Agent, or Firm* — Sughrue Mion, PLLC (57) ABSTRACT

The present invention relates to a therapeutic method and a diagnostic method using an antibody that binds to a ganglioside GM2 antigen, and a therapeutic agent and a diagnostic agent comprising as an active ingredient an antibody that binds to a ganglioside GM2 antigen. According to the present invention, the prognosis of GM2 positive mesothelioma patients can be improved by diagnosing and treating GM2 positive mesothelioma patients with a diagnostic agent and a therapeutic agent that comprise an anti-ganglioside GM2 antibody as an active ingredient.

22 Claims, 4 Drawing Sheets

(56) References Cited

OTHER PUBLICATIONS

Dufresne et al., "Mineral Fiber Content of Lungs in Patients with Mesothelioma Seeking Compensation in Quebec", American Journal of Respiratory and Critical Care Medicine, 1996, vol. 153, pp. 711-718.

Hakomori, "Aberrant Glycosylation in Cancer Cell Membranes as Focused on Glycolipids: Overview and Perspectives", Perspectives in Cancer Research, Jun. 1985, vol. 45, pp. 2405-2414.

Jennemann et al., "Glycosphingolipids of Human Gliomas", Cancer Research, Dec. 1, 1990, vol. 50, pp. 7444-7449.

Nakataki et al., "Novel Orthotopic Implantation Model of Human Malignant Pleural Mesothelioma (EHMES-10 Cells) Highly Expressing Vascular Endothelial Growth Factor and its Receptor", Cancer Science, Mar. 2006, vol. 97, No. 3, pp. 183-191.

Morinaga et al., "Asbestos-Related Lung Cancer and Mesothelioma in Japan", Industrial Health, 2001, vol. 39, pp. 65-74.

Barletta et al., "Complex Gangliosides Modulate the Integrin-Mediated Adhesion in a Rat Hepatoma Cell Line", Biochemical and Biophysical Research Communications, Apr. 15, 1993, vol. 192, No. 1, pp. 214-222.

Edakuni et al., "Restored Expression of the MYO18B Gene Suppresses Orthotopic Growth and the Production of Bloody Pleural Effusion by Human Malignant Pleural Mesothelioma Cells in SCID Mice", Oncology Research, 2006, vol. 16, pp. 235-243.

Hakomori, "Possible Functions of Tumor-Associated Carbohydrate Antigens", Current Opinion in Immunology, 1991, vol. 3, pp. 646-653.

Ikuta et al., "E7080, a Multi-Tyrosine Kinase Inhibitor, Suppresses the Progressions of a Malignant Pleural Mesothelioma with Different Proangiogenic Cytokine Production Profiles", Clinical Cancer Research, Dec. 1, 2009, vol. 15, No. 23, pp. 7229-7237.

Kurai et al., "Therapeutic Antitumor Efficacy of Anti-Epidermal Growth Factor Receptor Antibody, Cetuximab, Against Malignant Pleural Mesothelioma", International Journal of Oncology, 2012, vol. 41, pp. 1610-1618.

Yamada et al., "Genetically Engineered Humanized Anti-Ganglioside GM2 Antibody Against Multiple Organ Metastasis Produced by GM2-Expressing Small-Cell Lung Cancer Cells", Cancer Science, Dec. 2011, vol. 102, No. 12, pp. 2157-2163.

Yamada et al., "Lysophosphatidic Acid Stimulates the Proliferation and Motility of Malignant Pleural Mesothelioma Cells through Lysophosphatidic Acid Receptors, $LPA_1$, and $LPA_2$", Cancer Science, Aug. 2008, vol. 99, No. 8, pp. 1603-1610.

Moriya et al., "Antitumor Effect and Antiangiogenic Potential of the mTOR Inhibitor Temsirolimus against Malignant Pleural Mesothelioma", Spandidos Publications, Published online Dec. 30, 2013, 2 pages.

International Searching Authority, Search Report dated Mar. 4, 2014 in counterpart International Patent Application No. PCT/JP/2013/082621.

Seiji Yano et al., "Hito-ka Ganglioside GM2 Kotai ni yoru Shosaibo Hai Gan no Ten'i Yokusei Koka no Kento", Japanese Journal of Lung Cancer, 2001, vol. 41, No. 5, p. 481, E-14.

\* cited by examiner

| Sample ID | Age | Gender | Tissue Origin /Detected Tissue | Disease type by Pathological Classification | TNM Classification | Minimum Stage Grouping | Normal Tissue (%) | Lesion area (%) | Tumor Tissue (%) | Tumor/ Hyper- cellular Stroma (%) | Tumor/ Hypo- cellular or Acellular Stroma (%) | Necrosis (%) |
|---|---|---|---|---|---|---|---|---|---|---|---|---|
| FR0000 4AF8 | 62 | Male | Pleura / Lung | Mesothelioma of pleura, mixed type | pT3pN1pMX | III | 0 | 0 | 90 | 5 | 5 | 0 |
| FR0000 5932 | 68 | Male | Pleura / Pleura | Mesothelioma of pleura | pT3pN1pMX | III | 0 | 0 | 20 | 0 | 80 | 0 |
| FR0000 5E39 | 57 | Male | Pleura / Pleura | Mesothelioma of pleura | pTXpNXpMX | Not Reported | 0 | 0 | 70 | 15 | 15 | 0 |
| FR0001 7430 | 69 | Male | Pleura / Pleura | Mesothelioma of pleura | pT2pN0pMX | II | 0 | 0 | 90 | 5 | 5 | 0 |
| FR0001 A6C1 | 68 | Male | Pleura / Lung | Mesothelioma of pleura, mixed type | pT3pN1pMX | III | 0 | 0 | 35 | 20 | 45 | 0 |
| FR0001 CA2A | 65 | Male | Peritoneum / Colon | Mesothelioma of mesentery | Not Reported | Not Reported | 0 | 0 | 80 | 10 | 10 | 0 |
| FR0001 D4BA | 58 | Male | Pleura / Pleura | Mesothelioma of pleura, mixed type | pT2pN0pMX | II | 30 | 0 | 30 | 0 | 40 | 0 |
| FR0002 0029 | 69 | Male | Pleura / Pleura | Mesothelioma of pleura, mixed type | pT1pNXpMX | I | 0 | 0 | 60 | 20 | 20 | 0 |
| FR0002 081F | 53 | Male | Pleura / Lung | Mesothelioma of pleura | pT3pN1pM1 | IV | 0 | 0 | 65 | 0 | 35 | 0 |
| FR0002 65FD | 57 | Female | Pleura / Pleura | Mesothelioma of pleura | pT3pN1pMX | III | 0 | 0 | 85 | 0 | 15 | 0 |
| FR0002 731F | 73 | Male | Pleura / Pleura | Mesothelioma of pleura | pTXpNXpMX | Not Reported | 0 | 0 | 15 | 25 | 40 | 20 |
| FR0002 6B23 | 52 | Male | Pleura / Pleura | Mesothelioma of pleura, mixed type | pT3pN0pMX | III | 0 | 85 | 15 | 0 | 0 | 0 |
| FR0002 65A2 | 71 | Male | Pleura / Pleura | Mesothelioma of pleura, mixed type | pT4pNXpMX | IV | 0 | 0 | 50 | 0 | 50 | 0 |
| FR0002 939E | 50 | Male | Pleura / Pleura | Mesothelioma of pleura, mixed type | pT4pN0pMX | IV | 0 | 0 | 90 | 5 | 5 | 0 |
| FR0003 5469 | 65 | Male | Pleura / Pleura | Mesothelioma of pleura | pT2pN2pMX | III | 0 | 0 | 25 | 75 | 0 | 0 |
| FR0000 11E5 | 71 | Male | Lung / Lung | Mesothelioma of pleura | pT2pN0pMX | IIA | 20 | 0 | 20 | 60 | 0 | 0 |
| FR0000 2E6B | 81 | Male | Pleura / Chest wall | Mesothelioma of pleura, epithelial type | pTXpNXpMX | Not Reported | 0 | 0 | 85 | 0 | 15 | 0 |
| FR0000 6328 | 66 | Male | Pleura / Pleura | Mesothelioma of pleura | pT2pN0pMX | II | 0 | 0 | 55 | 35 | 10 | 0 |
| FR0000 6A38 | 86 | Male | Pleura / Pleura | Mesothelioma of pleura | pTXpNXpMX | Not Reported | 30 | 0 | 50 | 0 | 20 | 0 |
| FR0001 8ABD | 55 | Male | Pleura / Pleura | Mesothelioma of pleura | pT1pNXpMX | I | 0 | 0 | 50 | 0 | 50 | 0 |
| FR0001 6972 | 63 | Not Specified | Pleura / Pleura | Mesothelioma of pleura | pT1pNXpMX | I | 0 | 0 | 50 | 5 | 45 | 0 |
| SX0000 2843 | 61 | Male | Pleura / Abdominal wall | Mesothelioma of pleura, metastatic | pT4pNXpMX | IV | 0 | 0 | 40 | 20 | 40 | 0 |
| FR0001 742F | 69 | Male | Pleura / Pleura | Mesothelioma of pleura | pT2pN0pMX | II | 0 | 0 | 90 | 5 | 5 | 0 |
| FR0002 65FE | 57 | Female | Pleura / Pleura | Mesothelioma of pleura | pT3pN1pMX | III | 0 | 0 | 85 | 0 | 15 | 0 |
| FR0002 93A0 | 50 | Male | Pleura / Pleura | Mesothelioma of pleura, mixed type | pT4pN0pMX | IV | 0 | 0 | 90 | 5 | 5 | 0 |
| FR0000 2E64 | 81 | Male | Pleura / Chest wall | Mesothelioma of pleura, epithelial type | pTXpNXpMX | Not Reported | 10 | 0 | 55 | 0 | 35 | 0 |

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial
<220> FEATURE:
<223> OTHER INFORMATION: Description of the artificial sequence: HCDR1

<400> SEQUENCE: 1

Asp Tyr Asn Met Asp
1               5

<210> SEQ ID NO 2
<211> LENGTH: 17
<212> TYPE: PRT
<213> ORGANISM: Artificial
<220> FEATURE:
<223> OTHER INFORMATION: Description of the artificial sequence: HCDR2

<400> SEQUENCE: 2

Tyr Ile Tyr Pro Asn Asn Gly Gly Thr Gly Tyr Asn Gln Lys Phe Lys
1               5                   10                  15

Ser

<210> SEQ ID NO 3
<211> LENGTH: 11
<212> TYPE: PRT
<213> ORGANISM: Artificial
<220> FEATURE:
<223> OTHER INFORMATION: Description of the artificial sequence: HCDR3

<400> SEQUENCE: 3

Tyr Gly His Tyr Tyr Gly Tyr Met Phe Ala Tyr
1               5                   10

<210> SEQ ID NO 4
<211> LENGTH: 10
<212> TYPE: PRT
<213> ORGANISM: Artificial
<220> FEATURE:
<223> OTHER INFORMATION: Description of the artificial sequence: LCDR1

<400> SEQUENCE: 4

Ser Ala Ser Ser Ser Val Ser Tyr Met His
1               5                   10

<210> SEQ ID NO 5
<211> LENGTH: 7
<212> TYPE: PRT
<213> ORGANISM: Artificial
<220> FEATURE:
<223> OTHER INFORMATION: Description of the artificial sequence: LCDR2

<400> SEQUENCE: 5
```

Ser Thr Ser Asn Leu Ala Ser
1               5

<210> SEQ ID NO 6
<211> LENGTH: 9
<212> TYPE: PRT
<213> ORGANISM: Artificial
<220> FEATURE:
<223> OTHER INFORMATION: Description of the artificial sequence: LCDR3

<400> SEQUENCE: 6

Gln Gln Arg Ser Ser Tyr Pro Tyr Thr
1               5

<210> SEQ ID NO 7
<211> LENGTH: 120
<212> TYPE: PRT
<213> ORGANISM: Artificial
<220> FEATURE:
<223> OTHER INFORMATION: Description of the artificial sequence:
      humanized VH

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met Asp Trp Val Arg Gln Ala Pro Gly Gln Gly Leu Glu Trp Met
            35                  40                  45

Gly Tyr Ile Tyr Pro Asn Asn Gly Gly Thr Gly Tyr Asn Gln Lys Phe
50                  55                  60

Lys Ser Lys Val Thr Ile Thr Val Asp Thr Ser Thr Ser Thr Ala Tyr
65                  70                  75                  80

Met Glu Leu His Ser Leu Arg Ser Glu Asp Thr Ala Val Tyr Tyr Cys
                85                  90                  95

Ala Thr Tyr Gly His Tyr Gly Tyr Met Phe Ala Tyr Trp Gly Gln
            100                 105                 110

Gly Thr Leu Val Thr Val Ser Ser
        115                 120

<210> SEQ ID NO 8
<211> LENGTH: 108
<212> TYPE: PRT
<213> ORGANISM: Artificial
<220> FEATURE:
<223> OTHER INFORMATION: Description of the artificial sequence:
      humanized VL

<400> SEQUENCE: 8

Asp Ile Gln Leu Thr Gln Ser Pro Ser Ser Leu Ser Ala Ser Pro Gly
1               5                   10                  15

Asp Arg Val Thr Ile Thr Cys Ser Ala Ser Ser Val Ser Tyr Met
                20                  25                  30

His Trp Phe Gln Gln Lys Pro Gly Lys Ala Pro Lys Leu Trp Ile Tyr
            35                  40                  45

Ser Thr Ser Asn Leu Ala Ser Gly Val Pro Ser Arg Phe Ser Gly Ser
        50                  55                  60

Gly Ser Gly Thr Ser Tyr Ser Leu Thr Ile Ser Arg Leu Gln Pro Glu
65                  70                  75                  80

Asp Ile Ala Thr Tyr Tyr Cys Gln Gln Arg Ser Ser Tyr Pro Tyr Thr
                85                  90                  95

```
Phe Gly Gly Gly Thr Lys Val Glu Ile Lys Arg Thr
            100                 105
```

<210> SEQ ID NO 9
<211> LENGTH: 108
<212> TYPE: PRT
<213> ORGANISM: Artificial
<220> FEATURE:
<223> OTHER INFORMATION: Description of the artificial sequence: humanized VL

<400> SEQUENCE: 9

```
Asp Ile Gln Leu Thr Gln Ser Pro Ser Met Ser Ala Ser Pro Gly
1               5                   10                  15

Asp Arg Val Thr Ile Thr Cys Ser Ala Ser Ser Val Ser Tyr Met
                20                  25                  30

His Trp Phe Gln Gln Lys Pro Gly Lys Ser Pro Lys Leu Trp Ile Tyr
                35                  40                  45

Ser Thr Ser Asn Leu Ala Ser Gly Val Pro Ser Arg Phe Ser Gly Ser
            50                  55                  60

Gly Ser Gly Thr Ser Tyr Ser Leu Thr Ile Ser Ser Met Gln Pro Glu
65              70                  75                  80

Asp Phe Ala Thr Tyr Tyr Cys Gln Gln Arg Ser Ser Tyr Pro Tyr Thr
                85                  90                  95

Phe Gly Gln Gly Thr Lys Leu Glu Ile Lys Arg Thr
            100                 105
```

<210> SEQ ID NO 10
<211> LENGTH: 120
<212> TYPE: PRT
<213> ORGANISM: Artificial
<220> FEATURE:
<223> OTHER INFORMATION: Description of the artificial sequence: humanized VH

<400> SEQUENCE: 10

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met Asp Trp Val Lys Gln Ser Pro Gly Gln Gly Leu Glu Trp Met
                35                  40                  45

Gly Tyr Ile Tyr Pro Asn Asn Gly Gly Thr Gly Tyr Asn Gln Lys Phe
            50                  55                  60

Lys Ser Lys Val Thr Ile Thr Val Asp Thr Ser Thr Ser Thr Ala Tyr
65              70                  75                  80

Met Glu Leu His Ser Leu Arg Ser Glu Asp Thr Ala Val Tyr Tyr Cys
                85                  90                  95

Ala Thr Tyr Gly His Tyr Tyr Gly Tyr Met Phe Ala Tyr Trp Gly Gln
                100                 105                 110

Gly Thr Leu Val Thr Val Ser Ser
            115                 120
```

<210> SEQ ID NO 11
<211> LENGTH: 108
<212> TYPE: PRT
<213> ORGANISM: Artificial
<220> FEATURE:
<223> OTHER INFORMATION: Description of the artificial sequence: humanized VL

```
<400> SEQUENCE: 11

Asp Ile Gln Leu Thr Gln Ser Pro Ser Ser Leu Ser Ala Ser Pro Gly
1               5                   10                  15

Asp Arg Val Thr Ile Thr Cys Ser Ala Ser Ser Ser Val Ser Tyr Met
            20                  25                  30

His Trp Phe Gln Gln Lys Pro Gly Lys Ala Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Leu Gln Pro Glu
65                  70                  75                  80

Asp Ile Ala Thr Tyr Tyr Cys Gln Gln Arg Ser Ser Tyr Pro Tyr Thr
                85                  90                  95

Phe Gly Gly Gly Thr Lys Val Glu Ile Lys Arg Thr
            100                 105
```

THERAPEUTIC METHOD FOR MESOTHELIOMA

BACKGROUND OF THE INVENTION

1. Technical Field

The present invention relates to a therapeutic method and a diagnostic method using antibodies that bind to ganglioside GM2 antigen. The invention also relates to a therapeutic agent and a diagnostic agent that comprise antibodies that bind to ganglioside GM2 antigen as active ingredients.

2. Background Art

Gangliosides are a type of glycolipids composed of an extracellular sugar chain moiety containing a sialic acid, and a ceramide embedded in the lipid bilayer, and are expressed in a variety of patterns that varies according to cell type, organs, and animal species (Non-Patent Literature 1). It has been revealed that gangliosides have a wide range of biological functions, including intercellular recognition, control of cell proliferation via interaction with extracellular matrixs, and cell differentiation (Non-Patent Literatures 2 and 3).

Gangliosides are classified according to the patterns and the number of the sialic acid binding, and the presence or absence of N-acetylgalactosamine (GalNAc) and galactose (Gal) bound to the non-reducing end. GM2 is a member of ganglioside with the GalNAc$\beta$1-4(SA$\alpha$2-3)Gal$\beta$1-4Glc$\beta$1-1 Ceramide sugar chain structure.

It has been reported that ganglioside expression undergoes quantitative and qualitative changes with progression of cancer cells (Non-Patent Literature 4). It is also known that there is hardly any GM2 expression in normal cells, whereas high GM2 expression is observed in tumors such as lung cancer, neuroblastoma and glioma (Non-Patent Literatures 4 and 5). This has made GM2 an attractive target antigen in antibody cancer treatment.

Mesothelioma, also called a coated mesothelial tumor or mesothelial tumor, is a type of tumor that develops from mesothelium (such as pleura, peritonea and pericardium) of mesoderm origin, and is classified into localized benign tumors and diffuse malignant tumors. A form of malignant mesothelioma that occurs in pleura is malignant pleural mesothelioma (hereinafter, abbreviated to MPM in some cases).

MPM is a form of cancer that develops from the mesothelial cells of the thoracic cavity and is characterized by high growth rate, often accompanied by pleural effusion (Non-Patent Literature 6). Difficulty in breathing, short breath and cheat pain are some of the symptoms of MPM, and the quality of life (QOL) of the patients are lowered. Asbestos, iron, and simian virus 40 (SV40) are known examples of the causative substances of MPM (Non-Patent Literatures 7 and 8).

In particular, exposure to asbestos has been considered to be heavily associated with the onset of MPM, and people with a history of asbestos exposure are at significantly increased risk of MPM onset. Japan has imported and used a high volume of asbestos between 1970 and 1980 (Non-Patent Literature 9). Because the latency period of MPM is believed from 30 to 40 years after asbestos exposure, the morbidity rate of MPM in Japan is expected to greatly increase from 2010 to 2020.

Though the only treatment for MPM is the removal of tumor at early stages of onset, the disease is often found at the developed stages in the clinic. Further, MPM does not respond to common chemotherapy and radiation therapy, and has very poor prognosis with an average survival time of about 1 year from the onset. Accordingly, there is a need for a therapeutic method that can improve the prognosis of the disease.

CITATION LIST

Non-Patent Literatures

[Non-Patent Literature 1] J. Neurochem., 10, 613(1963)
[Non-Patent Literature 2] Curr. Opin. Immunol., 3, 646(1991)
[Non-Patent Literature 3] Biochem. Biophys. Res. Commun., 192, 214(1993)
[Non-Patent Literature 4] Cancer Res., 45, 2405(1985)
[Non-Patent Literature 5] Cancer Res., 50, 7444(1990)
[Non-Patent Literature 6] Cancer Sci., 97, 183(2006)
[Non-Patent Literature 7] Cell Mol. Biol., 17, 657(1997)
[Non-Patent Literature 8] Am. J. Respir. Crit. Care Med., 153, 711(1996)
[Non-Patent Literature 9] Industrial Health, 39, 65(2001)

SUMMARY OF THE INVENTION

Mesothelioma is treated by removing the tumor at early stages. However, the disease is often found at the progressed stages in the clinic, and does not respond well to common chemotherapy and radiation therapy. There is accordingly a need for a therapeutic method, a therapeutic agent, and a diagnostic method for improving the prognosis of the disease.

It is accordingly an object of the present invention to provide a therapeutic method, a therapeutic agent, and a diagnostic method that are effective for diagnosis and treatment of mesothelioma, and that can improve the prognosis of mesothelioma patients.

According to the present invention, the prognosis of GM2-positive mesothelioma patients can be improved by diagnosing and treating mesothelioma patients with a diagnostic agent and a therapeutic agent that comprise an anti-ganglioside GM2 antibody as an active ingredient.

BRIEF DESCRIPTION OF THE DRAWINGS

FIGS. 2 (a) and (b) represent the results of the evaluation of the ADCC activity of the anti-GM2 antibody against malignant mesothelioma cell line MSTO-211H. The vertical axis represents cytotoxicity (%), and the horizontal axis represents antibody concentration ($\mu$g/mL). Solid circle represents activity with the anti-GM2 antibody, and open circle represents activity with the negative control antibody (anti-DNP antibody). The results are presented for PBMC donor A [FIG. 2(a)] and donor B [FIG. 2(b)].

FIG. 4 represents human malignant mesothelioma tissue donor information, including, from the left, sample ID, age, gender, tissue origin (or detected tissue), disease type by pathological classification, TNM (tumor-node-metastasis) classification, minimum stage grouping, normal tissue %, lesion area %, tumor tissue %, tumor/hypercellular stroma %, tumor/hypocellular or acellular stroma %, and necrosis %.

DETAILED DESCRIPTION OF THE EXEMPLARY EMBODIMENTS

The present invention relates to (1) to (12) below.
(1) A method for treating or diagnosing mesothelioma, comprising using as an active ingredient an antibody or a fragment thereof that binds to a ganglioside GM2.
(2) The treating or diagnosing method described in (1), wherein the mesothelioma is one selected from pleural mesothelioma, peritoneal mesothelioma and pericardial mesothelioma.
(3) The treating or diagnosing method described in (2), wherein the pleural mesothelioma or the peritoneal mesothelioma is malignant pleural mesothelioma or malignant peritoneal mesothelioma.
(4) The treating or diagnosing method described in any one of (1) to (3), wherein the antibody is an antibody that binds to the α2-3 linked sialic acid (SA) of GM2.
(5) The treating or diagnosing method described in any one of (1) to (4), wherein the antibody is a monoclonal antibody.
(6) The treating or diagnosing method described in any one of (1) to (5), wherein the antibody is a recombinant antibody.
(7) The treating or diagnosing method described in (6), wherein the recombinant antibody is one selected from a chimeric antibody, a humanized antibody, and a human antibody.
(8) The treating or diagnosing method described in any one of (1) to (7), wherein the antibody is an antibody that comprises heavy chain (hereinafter, "H chain") complementarity determining regions (CDRs; hereinafter, abbreviated to "CDRs") 1 to 3 having the amino acid sequences of SEQ ID NOS: 1 to 3, respectively and light chain (hereinafter, "L chain") CDRs 1 to 3 having the amino acid sequences of SEQ ID NOS: 4 to 6, respectively.
(9) The treating or diagnosing method described in any one of (1) to (8), wherein the antibody is one selected from:

an antibody that comprises an H-chain variable region (hereinafter, referred to as "VH") having the amino acid sequence of SEQ ID NO: 7 and an L-chain variable region (hereinafter, referred to as "VL") having the amino acid sequence of SEQ ID NO: 8;

an antibody that comprises a VH having the amino acid sequence of SEQ ID NO: 7 and a VL having the amino acid sequence of SEQ ID NO: 9;

an antibody that comprises a VH having the amino acid sequence of SEQ ID NO: 10 and a VL having the amino acid sequence of SEQ ID NO: 8; and an antibody that comprises a VH having the amino acid sequence of SEQ ID NO: 10 and a VL having the amino acid sequence of SEQ ID NO: 11.
(10) The treating or diagnosing method described in any one of (1) to (9), comprising using at least one combination drug.
(11) The treating or diagnosing method described in (10), wherein the combination drug is at least one selected from a chemotherapeutic agent and a protein drug.
(12) A pharmaceutical composition comprising:

an antibody or a fragment thereof that binds to a ganglioside GM2; and a pharmaceutically acceptable carrier.

The present invention relates to a therapeutic agent and a diagnostic agent that comprise an anti-ganglioside GM2 antibody as an active ingredient, a therapeutic method that includes administering an anti-ganglioside GM2 antibody to a mesothelioma patient, and a method for diagnosing a mesothelioma patient with an anti-ganglioside GM2 antibody.

In the present invention, "mesothelioma" is also called a coated mesothelial tumor or mesothelial tumor, and refers to all tumors that develop from mesothelium (for example, pleura, peritonea, and pericardium) of mesoderm origin. Mesothelioma is classified into localized benign tumors and diffuse malignant tumors by the histological type, and these tumors are encompassed within the definition of mesothelioma according to the present invention.

Mesothelioma tumors of pleura origin are called pleural mesothelioma, and malignant tumors are called MPM. Mesothelioma tumors of peritonea origin are called peritoneal mesothelioma.

In the present invention, "ganglioside GM2" refers to a glucosylceramide with the GalNAcβ1-4(SAα2-3)Galβ1-4Glcβ1-1 Ceramide structure, and also will be referred to simply as "GM2". GalNAc, Gal, Glc and SA indicate N-acetylgalactosamine, galactose, glucose and sialic acid, respectively.

Examples of the anti-GM2 antibodies used in the present invention can include an anti-GM2 antibody that binds to an epitope comprising the α2-3 linked sialic acid (SA) of the GalNAcβ1-4(SAα2-3)Galβ1-4Glcβ1-1 Ceramide structure, an anti-GM2 antibody that binds to the epitope and shows effector activity, and an antibody that inhibits pleural effusion production in mesothelioma patients.

Other examples include antibodies that compete with any of the foregoing antibodies for the binding to GM2, antibodies that bind to the same epitope bound by the foregoing antibodies, and fragments of these antibodies.

Specifically, the antibody used in the present invention may be any one of the following antibodies:

Mouse monoclonal antibody KM750, and mouse monoclonal antibody KM796 described in JP-A-4-311385;

Monoclonal antibody MoAb5-3 described in Cancer Res., 46, 4116 (1986);

Monoclonal antibody MK1-16, and monoclonal antibody MK2-34 described in Cancer Res., 48, 6154 (1988);

Monoclonal antibody DMAb-1 described in J. Biol. Chem., 264, 12122 (1989);

Chimeric antibody DMF 10.167.4 antibody, and chimeric antibody ChGM2 described in WO2003/049704 and WO04/53102;

KM8966 produced by transformant KM8966 (FERM BP-5105), KM8967 produced by transformant KM8967 (FERM BP-5106), KM8969 produced by transformant KM8969 (FERM BP-5527), and KM8970 produced by transformant KM8970 (FERM BP-5528), described in JP-A-10-257893;

Antibody that comprises H chain CDRs 1 to 3 having the amino acid sequences of SEQ ID NOS: 1 to 3 and L chain CDRs 1 to 3 having the amino acid sequences of SEQ ID NOS: 4 to 6, respectively;

Antibody that comprises a VH having the amino acid sequence of SEQ ID NO: 7 and a VL having the amino acid sequence of SEQ ID NO: 8;

Antibody that comprises a VH having the amino acid sequence of SEQ ID NO: 7 and a VL having the amino acid sequence of SEQ ID NO: 9;

Antibody that comprises a VH having the amino acid sequence of SEQ ID NO: 10 and a VL having the amino acid sequence of SEQ ID NO: 8; and Antibody that comprises a VH having the amino acid sequence of SEQ ID NO: 10 and a VL having the amino acid sequence of SEQ ID NO: 11.

Antibodies that compete with these antibodies above for the binding to GM2, and antibodies that bind to the same epitopes bound by the foregoing antibodies also may be used in the present invention.

The anti-GM2 antibody used in the present invention can be any of a monoclonal antibody, an oligoclonal antibody and a polyclonal antibody, and is preferably a monoclonal antibody that binds to a single epitope.

The monoclonal antibodies used in the present invention can be monoclonal antibodies produced by hybridomas, or genetically recombinant antibodies produced by using gene recombinant techniques. For reduced immunogenicity in humans, it is preferable to use human chimeric antibodies (hereinafter, also referred to simply as "chimeric antibodies"), humanized antibodies [also referred to as human complementarity determining region (CDR) grafted antibodies], and human antibodies produced by using gene recombinant techniques.

As the antibodies used in the present invention, are humanized antibodies and human antibodies are preferably used among the above-mentioned antibodies.

The chimeric antibody is an antibody constructed from the VH and VL of non-human animal antibodies, and the heavy chain constant region (hereinafter, abbreviated to "CH") and the light chain constant region (hereinafter, abbreviated to "CL") of a human antibody. For the variable region, the type of animal is not particularly limited, as long as animals, such as mice, rats, hamsters, and rabbits, capable of producing hybridomas are used.

The human chimeric antibody can be produced by obtaining cDNAs encoding the VH and VL of a non-human animal antibody that specifically binds to GM2, inserting the cDNAs into an expression vector comprising genes that encode the CH and CL of a human antibody to construct an expression vector for the human chimeric antibody, and introducing the vector into an animal cell for expression. The CH of the human chimeric antibody is not particularly limited, as long as it is a human immunoglobulin (hereinafter, abbreviated to "hIg"). Preferably, the CH is of the hIgG class. The CL of the human chimeric antibody is not particularly limited, as long as it belongs to hIgG.

The humanized antibody is an antibody produced by grafting the complementarity determining regions (hereinafter, abbreviated to "CDRs") of the VH and VL of a non-human animal antibody to the VH and VL of a human antibody at appropriate locations. The human CDR grafted antibody can be produced by constructing cDNA that encodes a V region prepared by grafting the CDRs of the VH and VL of a GM2-specific non-human animal antibody to VH and VL frameworks (hereinafter, abbreviated to "FR") of any human antibody, inserting the cDNA into an expression vector comprising DNAs that encode the CH and CL of a human antibody to construct a expression vector for the humanaized antibody, and introducing the vector into an animal cell for expression. The amino acid sequences of the VH and VL FR of a human antibody are not particularly limited, as long as these are amino acid sequences derived from a human antibody.

The CH of the humanized antibody is not particularly limited, as long as it is hIg. Preferably, the CH is of the hIgG class. The CL of the humanized antibody is not particularly limited, as long as it belongs to hIg.

Specific examples of the humanized antibodies used in the present invention can include humanized antibodies having the CDR amino acid sequences, or the VH and VL amino acid sequences of antibodies selected from the following anti-GM2 antibodies:

Mouse monoclonal antibody KM750, and mouse monoclonal antibody KM796 described in JP-A-4-311385;

Monoclonal antibody MoAb5-3 described in Cancer Res., 46, 4116 (1986);

Monoclonal antibody MK1-16, and monoclonal antibody MK2-34 described in Cancer Res., 48, 6154 (1988);

Monoclonal antibody DMAb-1 described in J. Biol. Chem., 264, 12122 (1989); Chimeric antibody DMF 10.167.4 antibody, and chimeric antibody ChGM2 described in WO2003/049704 and WO04/53102; and KM8966 produced by transformant KM8966 (FERM BP-5105), KM8967 produced by transformant KM8967 (FERM BP-5106), KM8969 produced by transformant KM8969 (FERM BP-5527), and KM8970 produced by transformant KM8970 (FERM BP-5528), described in JP-A-10-257893.

More specific examples can include:

Humanized antibody that comprises H chain CDRs 1 to 3 having the amino acid sequences of SEQ ID NOS: 1 to 3 and L chain CDRs 1 to 3 having the amino acid sequences of SEQ ID NOS: 4 to 6, respectively;

Humanized antibody that comprises a VH having the amino acid sequence of SEQ ID NO: 7 and a VL having the amino acid sequence of SEQ ID NO: 8;

Humanized antibody that comprises a VH having the amino acid sequence of SEQ ID NO: 7 and a VL having the amino acid sequence of SEQ ID NO: 9;

Humanized antibody that comprises a VH having the amino acid sequence of SEQ ID NO: 10 and a VL having the amino acid sequence of SEQ ID NO: 8; and Humanized antibody that comprises a VH having the amino acid sequence of SEQ ID NO: 10 and a VL having the amino acid sequence of SEQ ID NO: 11.

The anti-GM2 antibody fragment contained in the therapeutic agent of the present invention can be a fragment of any of the foregoing antibodies. The type of antibody fragment is not particularly limited, and can be, for example, Fab, Fab', F(ab')$_2$, scFv, diabody, dsFv, or a peptide comprising CDR.

Fab is an antibody fragment having a molecular weight of about 50,000 and having antigen-binding activity, among fragments obtained by treating IgG antibody with papain (protease). The Fab of anti-GM2 antibody can be produced by treating the anti-GM2 antibody with papain, or by inserting a DNA encoding the Fab of the antibody into an expression vector, and introducing and expressing the vector in a procaryote or eukaryote.

F(ab')$_2$ is an antibody fragment having a molecular weight of about 100,000 and having antigen binding activity, among fragments obtained by treating IgG antibody with pepsin (protease). The F(ab')$_2$ of anti-GM2 antibody can be produced by treating the anti-GM2 antibody with pepsin, or by bonding Fab' (described below) with a thioether bond or a disulfide bond.

F(ab') is an antibody fragment of a molecular weight of about 50,000 and having antigen binding activity, in which the disulfide bond of the hinge region of the above F(ab')$_2$ is cleaved. F(ab') can be produced by treating F(ab')$_2$ of an antibody with dithiothreitol, or by inserting DNA encoding Fab' of the antibody into an expression vector and introducing this vector into prokaryote or eukaryote for expression.

scFv is an antibody fragment having antigen binding activity with a single VH and a single VL which are linked using a suitable peptide linker. scFv can be prepared by obtaining cDNAs encoding VH and VL of an antibody, constructing DNA encoding scFv, inserting this DNA into an expression vector, and introducing this expression vector into prokaryote or eukaryote for expression.

Diabody is an antibody fragment as a dimer formed of scFvs showing the same or different antigen binding specificity and this antibody fragment has a divalent antigen binding activity with respect to the same antigen or has divalent antigen binding activity with respect to two different types of antigens. Diabody may be produced by obtaining cDNAs encoding VH and VL of an antibody, constructing DNA encoding diabody, inserting this DNA into an expression vector, and introducing this expression vector into prokaryote or eukaryote for expression.

dsFv is an antibody fragment, in which 1 amino acid residue in each of VH and VL is substituted with a cystine residue, and the polypeptides are linked through a disulfide bond between these cysteine residues. dsFv can be prepared by obtaining cDNAs encoding VH and VL of an antibody, constructing DNA encoding dsFv, inserting this DNA into an expression vector, and introducing this expression vector into prokaryote or eukaryote for expression.

The peptide comprising CDR is a peptide comprising at least one or more regions of CDR of VH or VL. The peptide comprising CDR of an antibody can be produced by constructing DNA encoding CDR of VH and VL of the antibody, inserting this DNA into an expression vector, and introducing this expression vector into prokaryote or eukaryote for expression.

The peptide comprising CDR can be also produced by chemical synthesis method such as an Fmoc method (fluorenyl methyloxycarbonyl method) or a tBoc method (t-butoxycarbonyl method).

The anti-GM2 antibody used in the present invention has effector activity. In the present invention, "effector activity" refers to an activity induced via the Fc region of an antibody. Known examples thereof include antibody-dependent cellular cytotoxicity (ADCC activity), complement-dependent cytotoxicity (CDC activity), and antibody-dependent phagocytosis (ADP activity) by phagocytes such as macrophages and dendritic cells.

As a method for controlling the effector activity, a method of controlling the amount of the fucose (also called core fucose) which is bound to N-acetylglucosamine (GlcNAc) through α-1,6 bond in a reducing end of a complex-type N-linked sugar chain which is bound to asparagine (Asn) at position 297 according to EU index (Kabat et al, Sequence of Proteins of Immunological Interests, 5th edition, 1991) of an Fc region of an antibody (WO 2005/035586, WO 2002/31140, WO 00/61739), a method of controlling the activity by substituting amino acid residues of Fc region of the antibody, or the like is known.

The effector activity of the antibody can be increased or decreased by controlling the content of core fucose of the complex-type N-linked sugar chain bound to the Fc region of the antibody. The method for decreasing the content of fucose to be bound to the complex-type N-linked sugar chain bound to the Fc region of the antibody is to obtain an antibody having no core fucose binding to the complex-type N-linked sugar chain bound to the Fc region of the antibody (hereinafter, referred to as "non-fucosylated antibody") by expressing an antibody using CHO cell from which α1,6-fucosyltransferase gene (fucosyltransferase-8, FUT8) is deleted. It is accordingly preferable that the anti-GM2 antibody used in the present invention does not have a low core fucose content, or has no core fucose binding thereto.

The antibody to which no fucose has bound has a higher ADCC activity. On the other hand, as a method of increasing the content of fucose binding to the complex type N-linked sugar chain bound to Fc of an antibody, an antibody is expressed using a host cell to which α1,6-fucosetransferase gene has been introduced, whereby an antibody to which fucose has bound can be obtained. The ADCC activity of the antibody to which fucose has bound is lower than that of the antibody to which no fucose has bound.

ADCC activity or CDC activity can be increased or decreased by modifying amino acid residues in the Fc region of an antibody. Modifying amino acid residues in the Fc region increases or decreases the binding activity to FcγR, and enables the ADCC activity to be regulated. Modification of amino acid residues in the Fc region also increases or decreases the complement binding activity, and enables the CDC activity to be regulated.

For example, the CDC activity of an antibody can be increased by using the amino acid sequences of the Fc regions or CH described in the specifications of US Patent Application Publication No. 2007-0148165 and No. 2012-0010387. ADCC activity or CDC activity can be increased or decreased by modifying amino acid residues as described in the specifications of U.S. Pat. No. 6,737,056, No. 7,297,775, No. 7,317,091, and WO2005/070963.

The therapeutic agent of the present invention can treat a mesothelioma patient by being administered to a mesothelioma patient. Upon administration, the anti-GM2 antibody included as the active ingredient specifically binds to GM2 expressed on mesothelioma cells and exhibits various antitumor effects, including an inhibitory effect of mesothelioma cell growth, inhibitory effect of pleural effusion production and induction of ADCC activity by effector cells such as natural killer cells (NK cells). Therefore, as the therapeutic agent of the present invention, a mesothelioma therapeutic agent comprising the anti-GM2 antibody as an active ingredient can be exemplified.

The mesothelioma therapeutic agent of the present invention can be any therapeutic agent, as long as it comprises the anti-GM2 antibody as an active ingredient. Typically, the mesothelioma therapeutic agent of the present invention is preferably provided as a pharmaceutical preparation produced as a mixture with one or more pharmaceutically acceptable carriers by using a method well known in the field of pharmaceutics.

Preferably, an aseptic solution prepared by dissolving the antibody in an aqueous carrier such as an aqueous solution (e.g., water, saline, glycine, glucose, human albumin, or the like) is used. Further, a pharmaceutically acceptable additive such as a buffer or an isotonic agent (e.g., sodium acetate, sodium chloride, sodium lactate, potassium chloride, sodium citrate or the like) can be added to the preparation solution to close to physiological conditions. Further, it can be freeze-dried and then stored. If necessary, it can be dissolved in an appropriate solvent when using.

It is preferable that the therapeutic agent of the present invention is administered via the route being most effective for the treatment. Examples thereof may include oral administration and parenteral administration such as buccal, tracheal, intrarectal, subcutaneous, intramuscular, intraspinal, or intravenous administration. Among these, intraspinal or intravenous administration is preferred.

Examples of the preparation suitable for oral administration can include emulsions, syrups, capsules, tablets, powders, granules or the like. Liquid preparations such as emulsions and syrups can be produced using, as additives, water, sugars such as sucrose, sorbitol, fructose or the like, glycols such as polyethylene glycol, propylene glycol or the like, oils such as sesame oil, olive oil, soybean oil or the like, antiseptics such as p-hydroxybenzoate esters or the like, flavors such as strawberry flavor, peppermint, or the like. Capsules, tablets, powders, granules or the like can be produced using, as additives, excipients such as lactose, glucose, sucrose, mannitol or the like, disintegrating agents such as starch, sodium alginate or the like, lubricants such as magnesium stearate, talc or the like, binders such as polyvinyl alcohol, hydroxypropylcellulose, gelatin or the like, surfactants such as fatty acid ester or the like, plasticizers such as glycerin or the like.

Examples of the preparation suitable for parenteral administration can include injections, suppositories, sprays or the like. Injections can be prepared using a carrier such as a salt solution, a glucose solution and a mixture of both thereof. Suppositories can be prepared using a carrier such as cacao butter, hydrogenated fat, carboxylic acid or the like.

Sprays can be prepared using the antibody as it is, or using it together with a carrier which does not stimulate the buccal or airway mucous membrane of the recipient and can facilitate absorption of the antibody by dispersing it as fine particles or the like. Specific examples of the carrier may include lactose, glycerol or the like. It is possible to produce preparations such as aerosols and dry powders, depending on the properties of the antibody and the carriers used. In addition, the components exemplified as additives for oral preparations can also be added to the parenteral preparations.

The administration dose or frequency of the therapeutic agent of the present invention will vary depending on the desired therapeutic effect, the administration route, the period of treatment, age, body weights or the like. The administration dose for an adult person is typically 1 µg/kg to 10 mg/kg per day.

The therapeutic agent of the present invention encompasses a therapeutic agent that comprises the anti-GM2 antibody used in the present invention, and at least one combination drug.

Examples of the combination drug can include a chemotherapeutic agent, and a protein drug.

Examples of the chemotherapeutic agent can include doxorubicin, liposomal doxorubicin, cisplatin, carboplatin, vincristine, fludarabine, gemcitabine, pemetrexed, thalidomide, lenalidomide and pomalidomide. Preferred are cisplatin and pemetrexed.

Further, for example, E7080 that inhibits tyrosine kinase associated with angiogenesis also can be used as the combination drug.

Examples of the protein drug can include cytokines, and antibodies.

For example, the cytokines can be cytokines that activate effector cells of immunocompetent cells such as NK cells, macrophages, monocytes granulocytes, and derivatives of such cytokines.

Specific examples of the cytokines can include interleukin-2 (IL-2), interferons (IFN)-α, IFN-γ, IL-12, IL-15, IL-18, IL-21, fractalkine, macrophage-colony stimulating factors (M-CSF), GM-CSF, G-CSF, and tumor necrosis factors (TNF)-α, TNF-β, IL-1α and IL-1β, preferably IFN-γ is exemplified.

Examples of the antibodies may include therapeutic antibodies against mesothelioma targeted by the recombinant antibody that specifically binds to GM2 used in the present invention, angiogenesis inhibiting antibodies, antibodies that activate immunoactivity, fragments or fused antibodies of these antibodies.

Specific examples can include anti-CD40 antibodies (for example, SGN-40, and HCD122), anti-VEGF antibodies (such as bevacizumab), anti-IL-6R antibodies (specification of Japanese Patent No. 651541), anti-IL-6 antibodies (CNT0328), anti-CTLA4 antibodies (e.g., ipilimumab), and anti-CCR4 antibodies (e.g., mogamulizumab), or the like.

Examples of the antibodies or antibody fragments of the present invention may include antibodies or antibody fragments that are conjugated to the drugs that can be used concurrently.

The therapeutic agent of the present invention can be used to treat tissues that have developed mesothelioma as long as the mesothelioma is expressing GM2, nevertheless benign or malignant. The present invention also includes a combination therapy in which the therapeutic agent for mesothelioma comprising the anti-GM2 antibody as an active ingredient and the combination drug are simultaneously or separately administered.

The present invention also includes a method for treating a mesothelioma patient that includes administering the anti-GM2 antibody as an active ingredient. The method for treating a mesothelioma patient of the present invention also includes a combination therapy for treating a mesothelioma patient in which at least one combination drug is administered to a mesothelioma patient, simultaneously with or separately from administration of the active ingredient anti-GM2 antibody. In the combination therapy, the anti-GM2 antibody and the combination drug can be administered in any order and can be appropriately decided according to the stage and the conditions of a mesothelioma patient.

The mesothelioma treatment method of the present invention can inhibit mesothelioma cell proliferation and pleural effusion production as a result of the specific binding of the anti-GM2 antibody to GM2-expressing mesothelioma cells. By the specific binding of the anti-GM2 antibody to GM2-expressing mesothelioma cells, the mesothelioma treatment method of the present invention also can exhibit cytotoxicity against mesothelioma cells with the ADCC activity mediated by effector cells such as natural killer cells (NK cells) present in the patient's body, inhibit mesothelioma cell proliferation and pleural effusion production.

The present invention thus also includes a method for inhibiting mesothelioma cell proliferation, a method for inducing cytotoxicity in mesothelioma cells, and a method for inhibiting pleural effusion production with the anti-GM2 antibody.

The effectiveness of the therapeutic method and the therapeutic agent of the present invention can be examined by in vivo anti-tumor activity assay using an animal model.

Examples of the animal model can include a xenograft model prepared by grafting a cultured cell line derived from human cancer tissues into a mouse. The xenograft model may be produced by grafting a human cancer cell line to various sites of an immunodeficient mouse such as SCID mice, for example, subcutaneously, intradermally, intrathoracically, intrapericardially, intraperitoneally, or intravenously.

The animal model can be used to evaluate the effectiveness of the therapeutic agent of the present invention, including the effectiveness of single administration of the antibody, and the effectiveness of combined administration with a combination drug.

The present invention also includes a method for diagnosing mesothelioma with the anti-GM2 antibody. A patient with mesothelioma involving GM2 can be diagnosed by detecting or assaying GM2, or cells and/or tissues expressing GM2, with the anti-GM2 antibody or fragments thereof.

First, biological samples collected from the bodies of healthy individuals are used to detect or assay GM2 with the anti-GM2 antibody or fragments or derivatives thereof using an immunological technique (described below), and determine the GM2 amount in the biological samples from these healthy individuals.

GM2 level is also determined for a subject's biological sample, and compared with those of the healthy individuals. The subject is diagnosed with mesothelioma when its GM2 level is higher than those of the healthy individuals.

The immunological technique refers to a technique that detects or assays antibody or antigen levels using labeled antigens or antibodies. For example, radioimmunoassay, enzyme immunoassay, fluorescent immunoassay, luminescent immunoassay, western blotting, a physiochemical technique, or the like is used.

In the radioimmunoassay, for example, the anti-GM2 antibody or fragments thereof are reacted with antigens or antigen-expressing cells, and further reacted with radiolabeled anti-immunoglobulin antibodies or binding fragments. Then, measurement with a scintillation counter or the like is performed.

In the enzyme immunoassay, for example, the anti-GM2 antibody or fragments thereof are reacted with antigens or antigen-expressing cells, and further reacted with labeled anti-immunoglobulin antibodies or binding fragments. The generated color is then measured with an absorption spectrometer. For example, sandwich ELISA can be used.

As a label used in the enzyme immunoassay, any known enzyme label [Enzyme Immunoassay, IGAKU-SHOIN Ltd. (1987)] can be used. Examples thereof include alkaline phosphatase labeling, peroxidase labeling, luciferase labeling, biotin labeling or the like. Sandwich ELISA is a method in which an antibody is bound to a solid phase, antigen to be detected or measured is trapped and another antibody is allowed to react with the trapped antigen.

In the ELISA, two kinds of antibodies which recognize the antigen to be detected or measured or the antibody fragment thereof in which antigen recognizing site is different are prepared and one antibody or antibody fragment is previously adsorbed on a plate (e.g., 96-well plate) and another antibody or antibody fragment is labeled with a fluorescent substance such as FITC, an enzyme such as peroxidase, or biotin, or the like.

The plate to which the above antibody is adsorbed is allowed to react with the cell or lysate thereof, tissue or disintegrated solution thereof, cell culture supernatant, serum, pleural effusion, ascitic fluid, ocular fluid or the like, separated from living body, then allowed to react with labeled monoclonal antibody or antibody fragment and a detection reaction according to the labeled substance is carried out. An antigen concentration in the test sample can be calculated from a calibration curve prepared by a stepwise dilution of antigen of known concentration.

For example, ELISA can be performed for GM2 in the following manner. GM2 is dissolved in an ethanol solution containing phosphatidylcholine and cholesterol. The solution is then dispensed in each well of a microtiter plate, and blocking with bovine serum albumin (BSA)-containing phosphate buffer saline (PBS) (hereinafter, abbreviated to "BSA-PBS") is performed after being air dried. GM2 antibody is then reacted thereto, and a secondary antibody labeled with an appropriate enzyme is further reacted thereto, thereby determining the GM2 level.

As an antibody used for sandwich ELISA, any of a polyclonal antibody and a monoclonal antibody can be used or antibody fragments such as Fab, Fab' and F(ab)$_2$ may be used.

As a combination of two kinds of antibodies used in sandwich ELISA, a combination of monoclonal antibodies or antibody fragments recognizing different epitopes can be used or a combination of polyclonal antibody with monoclonal antibody or antibody fragments can be used.

A fluorescent immunoassay includes a method described in the literatures [Monoclonal Antibodies—Principles and practice, Third Edition, Academic Press (1996); Manual for Monoclonal Antibody Experiments, Kodansha Scientific (1987)] or the like. As a label used for the fluorescent immunoassay, any of known fluorescent labels [Fluorescent Immunoassay, Soft Science, (1983)] can be exemplified. For example, fluorescent isothiocyanate (FITC), RITC, Cy3, Cy5, Alexa, or the like is used.

The luminescent immunoassay is carried out using the methods described in the literature [Bioluminescence and Chemical Luminescence, clinical test, 42, Hirokawa Shoten (1998)] or the like. As a label used for luminescent immunoassay, any of known luminescent labels can be exemplified. Examples thereof can include acridinium ester, lophine or the like.

Western blotting is carried out as follows. An antigen or a cell expressing an antigen is fractionated by SDS (Sodium dodecyl sulfate)-PAGE [Antibodies-A Laboratory Manual Cold Spring Harbor Laboratory, (1988)]. Then, the gel is blotted onto a polyvinylidene fluoride (PVDF) membrane or nitrocellulose membrane, and the membrane is allowed to react with antigen-recognizing antibody or antibody fragment. Further, it is allowed to react with an anti-mouse IgG antibody or antibody fragment which is labeled with a fluorescent substance such as FITC, an enzyme label such as peroxidase, a biotin label, or the like. After the reaction, the label is visualized to measure. An example thereof is described below.

Cells or tissues expressing GM2 are lysed, and electrophoresed in a protein amount of 0.1 to 30 μg per lane under reduced conditions using SDS-PAGE. The electrophoresed proteins are transferred to a PVDF membrane, which is then placed in 1 to 10% BSA-containing PBS (hereinafter, referred to as "BSA-PBS") at room temperature for 30 min for blocking.

The monoclonal antibody of the present invention is then allowed to react therewith. After washing with PBS containing 0.05 to 0.1% of Tween-20 (hereinafter, referred to as "Tween-PBS"), a reaction with peroxidase-labeled goat anti-mouse IgG is performed at room temperature for 2 hours.

It is washed with Tween-PBS, and bands bound to the monoclonal antibody are detected with, for example, ECL® Western Blotting Detection Reagents (manufactured by Amersham), thereby detecting GM2. Antibodies that can bind to GM2 are used for the western blotting detection.

In the physiochemical technique, for example, an agglutinate is formed by the binding of the antigen GM2 and the anti-GM2 antibody or fragments thereof, and the agglutinate is detected. The physiochemical technique also can be performed using methods such as the capillary technique, single immunodiffusion, immunonephelometry, and latex-enhanced immunoturbidimetry [An Outline of Clinical Test Methods, Kanehara & Co., Ltd. (1998)].

In a latex immunoturbidimetry method, a carrier such as polystyrene latex having a particle size of about 0.1 to 1 μm sensitized with antibody or antigen can be used and when an antigen-antibody reaction is carried out using the corresponding antigen or antibody, scattered light in the reaction solution increases while transmitted light decreases. By detecting such a change as absorbance or integral sphere turbidity, it is possible to measure antigen concentration, or the like. in the test sample.

Known immunodetection techniques can be used for the detection or assay of GM2-expressing cells. Immunoprecipitation, immunocytochemistry, immunohistostaining, fluorescent antibody staining, or the like are preferably used.

In the immunoprecipitation, GM2-expressing cells or GM2-containing tissue extracts are reacted with the anti-GM2 antibody or fragments thereof, and a carrier capable of specifically binding to immunoglobulins such as protein G-sepharose is added to precipitate an antigen-antibody complex. It also can be performed in the following manner.

The monoclonal antibody or fragments thereof of the present invention are immobilized on an ELISA 96-well plate, and blocking with BSA-PBS is performed. When the antibody is in an unpurified state, for example, such as in a hybridoma culture supernatant, the hybridoma culture supernatant is dispensed for binding after immobilizing, for example, an anti-mouse immunoglobulin, an anti-rat immunoglobulin, protein-A, or protein-G on the ELISA 96-well plate, and blocking the plate with BSA-PBS.

After discarding the BSA-PBS, it is thoroughly washed with PBS, and reacted with a lysate of GM2-expressing cells or tissues. After thoroughly washing the plate, immunoprecipitates are extracted with an SDS-PAGE sample buffer, and detected by western blotting.

In the immunocytochemistry and immunohistostaining, antigen-expressing cells or tissues are reacted with the anti-GM2 antibody after being optionally treated with a surfactant or methanol for improved antibody permeability. After further reaction with anti-immunoglobulin antibodies or binding fragments thereof labeled with a fluorescent label such as FITC, an enzyme label such as peroxidase, biotin, or the like, the labels are visualized, and observed with a microscope.

Detection also can be performed by using the fluorescent antibody staining that involves reaction of fluorescence-labeled antibodies and cells, and a flow cytometer analysis [Monoclonal Antibodies-Principles and practice, Third edition, Academic Press (1996), and Monoclonal Antibody Experiment Manual, Kodansha Scientific (1987)]. Specifically, the anti-GM2 antibody or fragments thereof used in the present invention can be used for detection of GM2 expressed on cell membrane, using fluorescent antibody staining.

Further, when the FMAT 8100 HTS System (Applied Biosystems) is used for fluorescent antibody staining, antigen or antibody levels can be measured without separating free antibodies or antigens that are not involved in the formation of the antibody-antigen complex from the antibody-antigen complex.

EXAMPLES

The present invention is described below using Examples. However, the present invention is not limited by the following Examples.

Example 1

Analysis of GM2 Expression in Malignant Mesothelioma Cell Lines by Flow Cytometry (FCM)

Malignant mesothelioma cell lines NCI-H226 (CRL-5826), MSTO-211H (CRL-2081) and NCI-H2452 (CRL-5946) were obtained from American Type Culture Collection (ATCC). Malignant mesothelioma cell line ACC-MESO-1 (RCB-2292) was obtained from Riken Cell Bank. These were used for experiments (Cancer Sci 2006; 97: 387-394).

The four malignant mesothelioma cell lines were released with 0.02% EDTA solution, and the cells were washed with phosphate buffer saline (PBS), and suspended in a buffer (hereinafter, abbreviated to "FCM buffer") prepared by adding 0.05% $NaN_3$ and 0.02% EDTA to PBS containing 1% bovine serum albumin (BSA) (hereinafter, abbreviated to "BSA-PBS").

The anti-GM2 antibody was produced from the anti-GM2 humanized antibody (specifications of Japanese Patent No. 4550947 and U.S. Pat. No. 6,872,392) that has the amino acid sequences of SEQ ID NOS: 10 and 11 for VH and VL, respectively, using α1,6-fucosyltrasferase (FUT8) genomic gene knock-out CHO cells (WO2005/035586), and was used.

The cell suspension was dispensed in a U-bottom 96-well plate ($2\times10^5$ cells/50 μL/well). Test samples were prepared by adding 10 μg/mL of the anti-GM2 humanized antibody or anti-dinitrophenylhydrazine (DNP) antibody (negative control; Motoki et al., Clin. Cancer Res., 11, 3126-3135, 2005) to the plate in 50 μL/well after dilution with FCM buffer. Then, the mixtures were allowed to react on ice for 1 hour.

Figure 1:
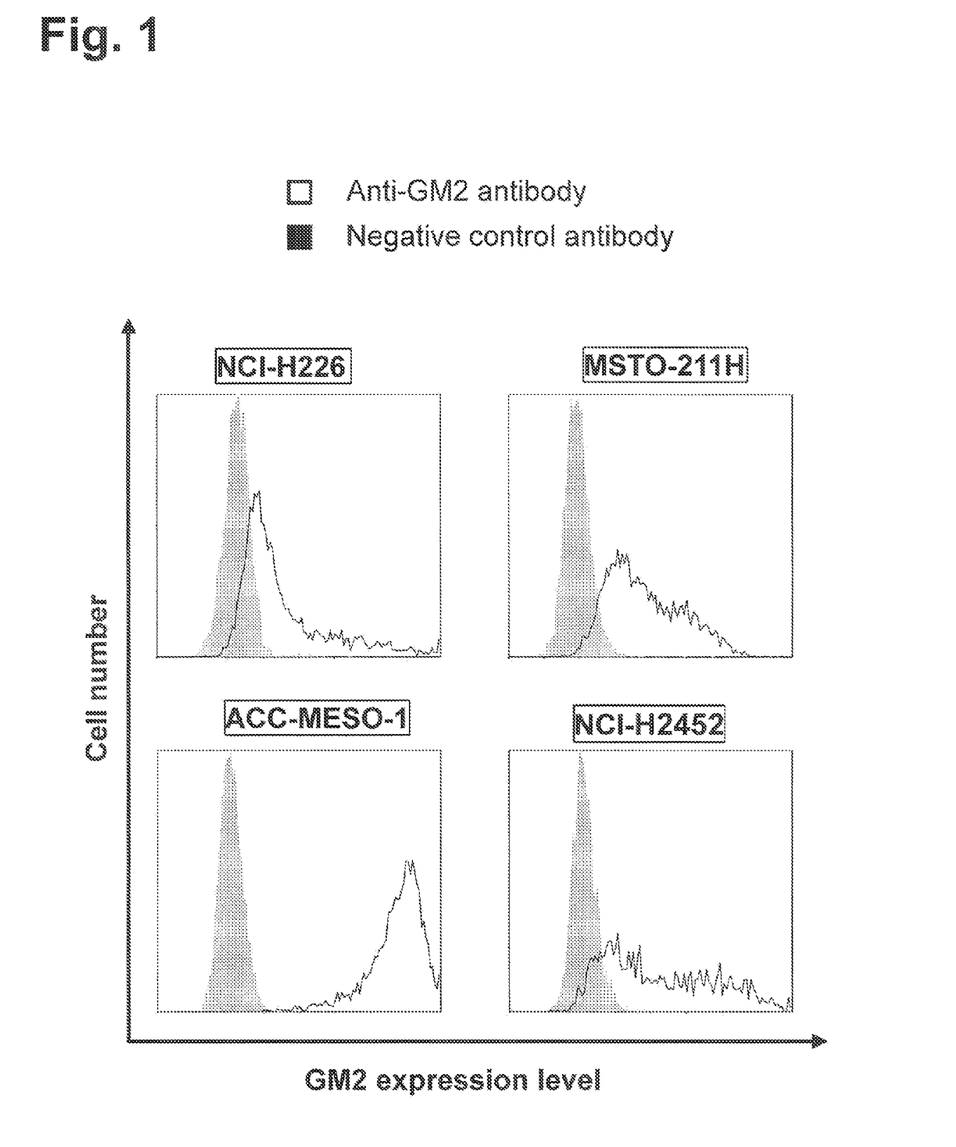
FIG. 1 is a histogram representing the flow cytometry analysis result of GM2 expression in malignant mesothelioma cell lines. The horizontal axis represents GM2 expression level, and the vertical axis represents cell count. The solid histogram and the grey histogram represent reaction with an anti-GM2 antibody and a negative control antibody, respectively.

The cells were washed three times with PBS, and Alexa Fluor488 goat anti-human IgG (H+L) (Molecular Probes) was added as secondary antibody in 50 μL/well after being diluted 300 times. Then, the mixtures were allowed to react on ice for 30 min in the dark. The cells were suspended in PBS after being washed again three times with PBS. The 510 to 530 nm fluorescence intensity excited by a 488-nm argon-ion laser was measured using a flow cytometer (Cytomics Fc500 MPL/Beckman Coulter). The results are shown in FIG. 1.

As a result, the anti-GM2 antibody was shown to be reactive to the all malignant mesothelioma cell lines. The mean fluorescence intensity (MFI) values of the anti-GM2 antibody and the anti-DNP antibody reacting to each cell were NCI-H226 (33, 1.5), MSTO-211H (18.8, 1.03), ACC-MESO-1 (298, 1.17), and NCI-H2452 (57.9, 1.24). GM2 expression was thus found in all of the four malignant mesothelioma species.

These results indicate that GM2 is expressed in malignant mesothelioma also in the clinic, and demonstrate that the anti-GM2 antibody is actually useful for the treatment or diagnosis of malignant mesothelioma.

Example 2

Antibody-Dependent Cellular Cytotoxicity (ADCC Activity) Assay 2.1 Preparation of Target Cell Suspension Malignant mesothelioma cell line MSTO-211H was collected, and washed with phenol red-free RPMI-1640 medium containing 5% fetal bovine serum (FBS) (manufactured by WAKO; hereinafter, abbreviated to "ADCC assay medium"). A cell suspension ($1\times10^4$ cells/50 μL) was prepared using the same medium.

2.2 Preparation of Effector Cell Suspension

Frozen human peripheral blood mononuclear cells (MNC) purchased from AllCells Corporation were used as effector cells. The frozen MNC was thawed and suspended in a medium prepared by adding 50 μL of DNase I (DNase I recombinant, RNase-free, manufactured by Roche) to 20 mL of RPMI1640 medium containing 10% fetal calf serum (FCS), penicillin, streptomycin, glutamine, non-essential amino acid (NEAA), pyruvic acid, and Hepes (all available from Invitrogen; hereinafter, abbreviated to "recovery medium").

After centrifugation (450×g, 10 min), the cells were resuspended in a 20 mL recovery medium and allowed to stand at 37° C. for 2 hours under 5% $CO_2$ condition. The resulting peripheral blood mononuclear cells (PBMC) were washed twice with ADCC assay medium, and an effector cell suspension was prepared in $1\times10^6$ cells/50 μL using the same medium.

2.3 ADCC Activity Assay

An anti-GM2 antibody or anti-DNP antibody (negative control) solution of desired concentrations was dispensed in each well of a U-bottom 96-well plate (50 μL/well), and the target cell suspension (50 μL) prepared in 2.1 above, and the effector cell suspension (50 μL) prepared in 2.2 above were added in an effector cell (E)-to-target cell (T) ratio (E/T ratio) of 100. The total volume was adjusted to 150 μL by adding ADCC assay medium.

After centrifugation (50×g, 3 min), a reaction was allowed at 37° C. for 4 hours. After the reaction, the cells were recentrifuged (50×g, 5 min), and the lactate dehydrogenase (LDH) activity in the supernatant was measured with CytoTox 96 Non-Radioactive Cytotoxicity Assay (Promega) according to the manufacture's protocol.

ADCC activity was determined from the following equation.

Cytotoxicity (%)=([absorbance of sample]−([absorbance of effector cell spontaneous release]+[absorbance of target cell spontaneous release]))/([absorbance of total target cell release]−[absorbance of target cell spontaneous release])×100

Here, the target cell spontaneous release value was obtained by measuring the absorbance of each well prepared by addition of the target cell solution (50 μL) and the medium (100 μL). The target cell and effector cell spontaneous release value was obtained by measuring the absorbance of each well prepared by addition of the target cell solution, the effector cell solution, and the medium (50 μL each).

Figure 2:
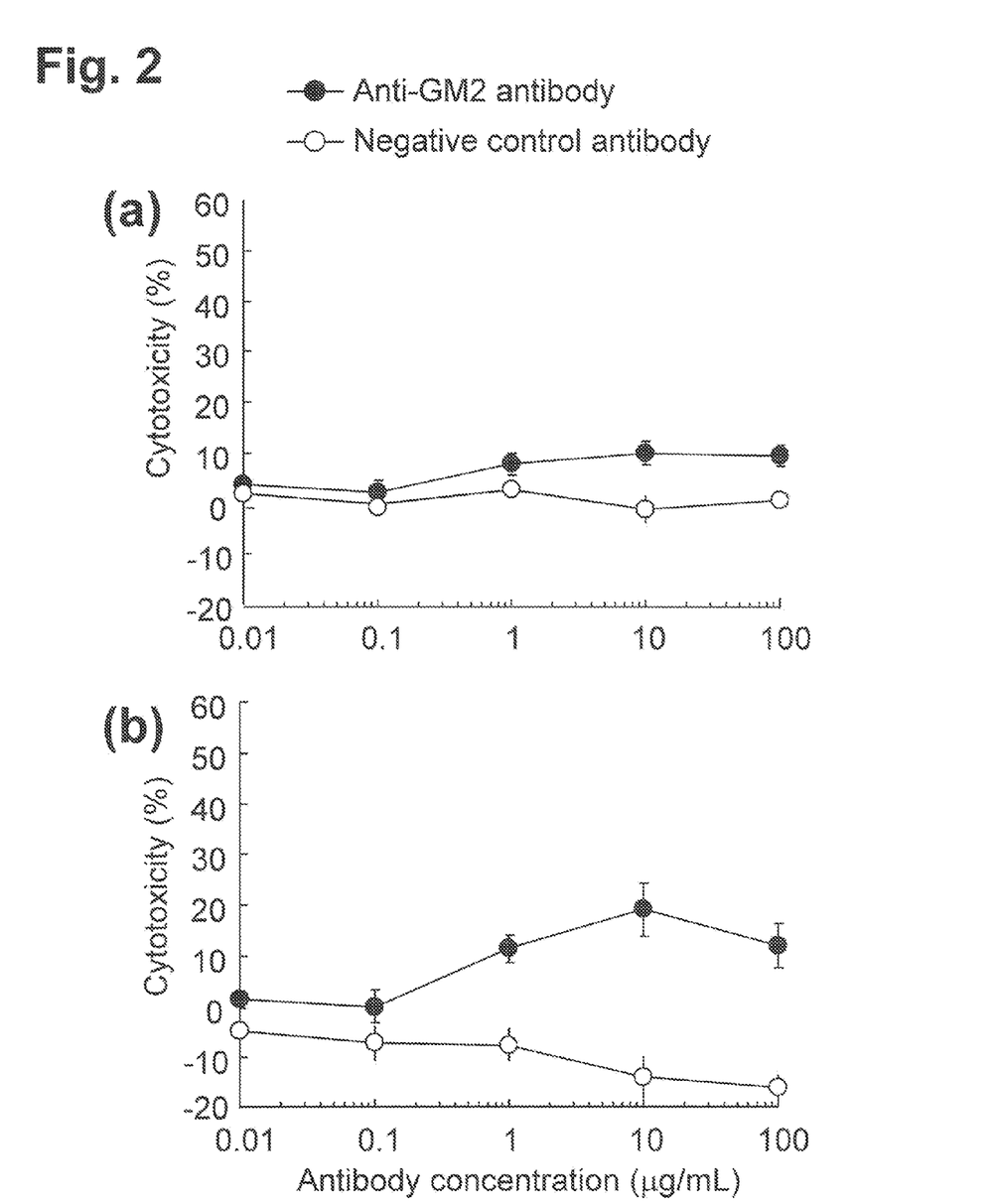

The total target cell release value was obtained in a similar way from wells to which the Lysis Solution (15 μL) attached to the kit was added 45 minutes before the end of the reaction performed after adding the target cell solution (50 μL) and the medium (85 μL). The results are shown in FIGS. 2(a) and (b).

As a result, the malignant mesothelioma cell line MSTO-211H was injured in a manner that depended on the concentration of the anti-GM2 antibody. It was thus confirmed that the anti-GM2 antibody exhibits ADCC activity against the malignant mesothelioma cells.

These results indicate that the anti-GM2 antibody administered to a malignant mesothelioma patient can exhibit cytotoxicity to the cancer cells via the effector cells present in the patient's body.

Example 3

Efficacy Evaluation of Anti-GM2 Antibody Using Malignant Mesothelioma Cell Line MSTO-211H Orthotopic Graft Model in SCID Mice Anti-TM-β1 antibody (300 μg; anti-mouse IL-2 receptor β chain antibody) [J. Immunol., 147, 2222 (1991)] was administered to SCID mice (CLEA Japan) 2 days before grafting cancer cells. On the day of cancer cell transplantation, each mouse was anesthetized with ether, and shaved to remove hair from the right chest wall. The skin and the subcutaneous tissue were cut open to expose the parietal pleura. The MSTO-211H cell suspension ($1\times10^6$ cells/100 μL) was then administered into the thoracic cavity through the parietal pleura using a 27 G syringe, and the cut was sutured.

In order to evaluate the mesothelioma therapeutic effect of the anti-GM2 antibody, the anti-GM2 human antibody (10 μg) was intravenously administered on day 7 and 14 post cancer cell transplantation.

Figure 3:
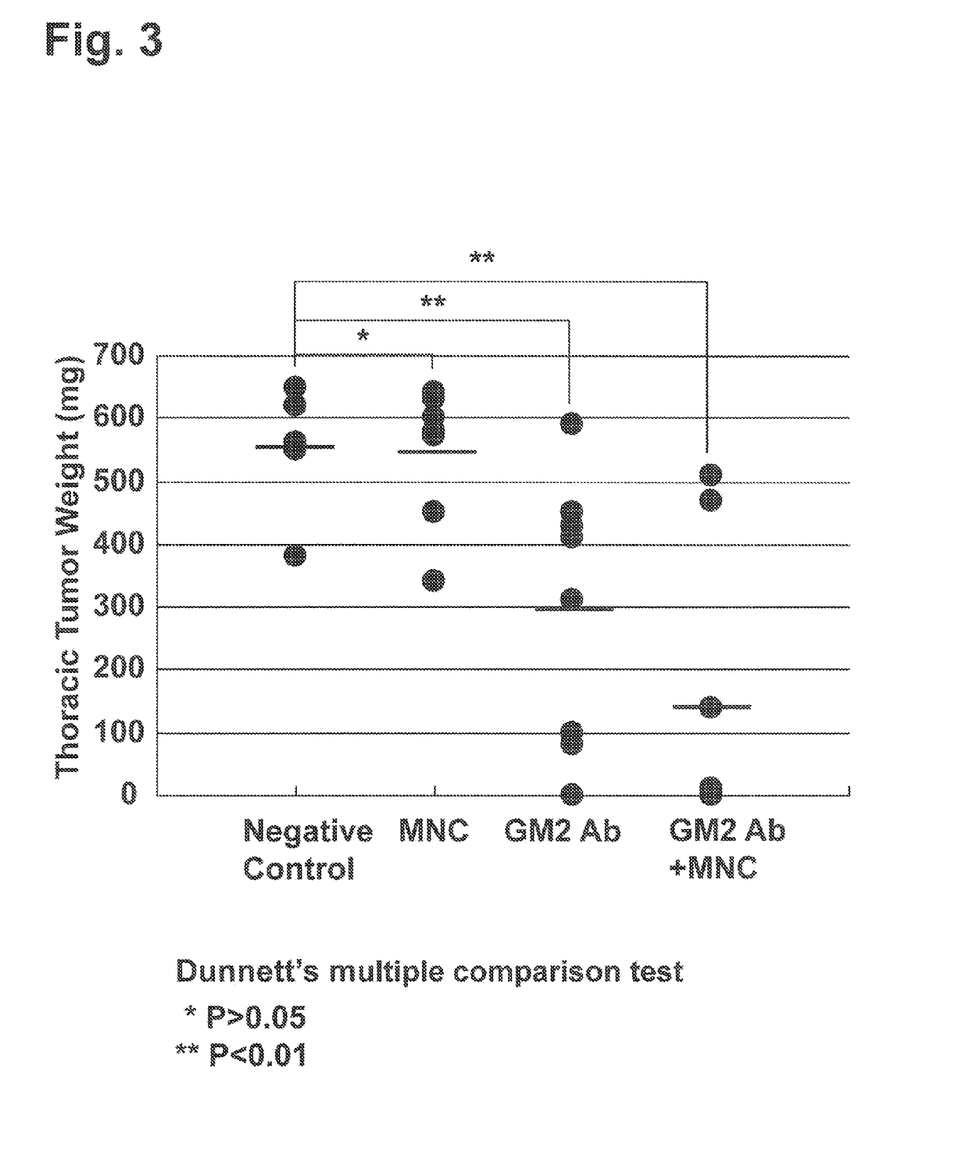
FIG. 3 represents the result of the evaluation of the anti-tumor effect of the anti-GM2 antibody in an SCID mouse orthotopic graft model using malignant mesothelioma cell line MSTO-211H. The vertical axis represents thoracic tumor mass (mg), and the horizontal axis represents the type of administered samples. Solid circle represents individual thoracic tumor mass (mg), and the horizontal bar represents mean value. Statistical significant difference was determined by performing a Dunnett's multiple comparison test.

Further, for the evaluation of the contribution by the human immune cells, human mononuclear cells (MNC; $1\times10^6$ cells) separated from the peripheral blood of a healthy individual with Lymphocyte Separation Medium (LSM) were intravenously administered on day 7 and 14 post cancer cell transplantation. The mice were killed on day 21 post transplantation, and examined for the presence or absence of a thoracic tumor, tumor size, the presence or absence of a pleural effusion, and the amount of pleural effusion. Statistical significant difference was determined by performing a Dunnett's multiple comparison test. The results are shown in FIG. 3 and Table 1.

TABLE 1

| Treatment | Dose | Thoracic tumor | | | Pleural effusion | | |
| | | Incidence | Median Mass (mg) | Range | Incidence | Median Volume (μL) | Range |
| --- | --- | --- | --- | --- | --- | --- | --- |
| Control | DW | 8/8 | 550 | 380-650 | 3/8 | 0 | 0-300 |
| MNC | $1\times10^6$ cells | 8/8 | 590 | 380-640 | 2/8 | 0 | 0-200 |
| GM2A b | 10 μg | 7/8 | 360* | 0-590 | 1/8 | 0 | 0-250 |
| GM2A b + MNC | 10, $1\times10^6$ cells | 4/8 | <10* | 0-510 | 1/8 | 0 | 0-150 |

As a result, the incidence of thoracic tumor, and the average tumor mass were significantly smaller in the anti-GM2 antibody-administered mice than in the antibody non-administered mice and the human MNC only administered mice. The incidence of pleural effusion accumulation was also lowered.

The mice administered with both the anti-GM2 antibody and the human MNC had lower incidences of thoracic tumor, and smaller average tumor masses than mice administered with the human MNC or the anti-GM2 antibody. The result that anti-tumor effect was not observed in the sole administration of the human MNC suggested that the human MNC enhanced the anti-tumor effect of the anti-GM2 antibody, and improved efficacy.

These results suggested the potential effectiveness of the anti-GM2 antibody for malignant mesothelioma patients.

Example 4

GM2 Expression in SCID Mouse Malignant Mesothelioma Cell Line MSTO-211 H Orthotopic Graft Model A tumor block was removed from the chest region of the human malignant mesothelioma cell line MSTO-211H-grafted mice, and embedded in an OCT compound. The embedded block was cut into about a 6-μm slices, and frozen tissue slices were produced. Then immunohistochemical staining was performed as follows.

(1) The tissue slices were fixed in anhydrous acetone at room temperature for 5 min, and air dried for 30 min.
(2) The tissue slices were washed in running water for 5 min.
(3) The tissue slices were fixed in a 1:10 diluted concentration of MORPHOSAVE at room temperature for 15 min, and washed twice with PBS for 5 min.

(4) The tissue slices were allowed to react in an endogenous peroxidase blocking solution (2 U/mL glucose oxidase, 10 mmol/L glucose, 1 mmol/L sodium azide) at 37° C. for 60 min, and washed twice with PBS for 5 min.
(5) The tissue slices were allowed to react in BSA-PBS (1 w/v % BSA in PBS) at room temperature for 10 min.
(6) The anti-GM2 antibody (primary antibody) was mixed with an equal amount of a secondary antibody [(peroxidase-conjugated affinipure donkey anti-human IgG (H+L)] (Jackson Immuno Research Laboratories) used in 1.5 times the concentration of the primary antibody, and the mixture was reacted with the tissue slices overnight at 4° C.

Thereafter, IgG from human serum (manufactured by Sigma-Aldrich) of 100 times the concentration of the secondary antibody was added, and a reaction was allowed in the solution at 4° C. for 2 hours to produce a precomplex mixture. The tissue slices in the precomplex mixture were allowed to react at room temperature for 2 hours, and washed three times with PBS for 5 min.
(7) The tissue slices were allowed to react in a solution (DAB substrate chromogen) prepared by dissolving 15 mg of a DAB tablet in PBS (100 mL), and adding 33.3 μL of a 30% hydrogen peroxide solution at room temperature for 2 min, and washed three times with PBS for 5 min.
(8) The tissue slices were reacted in hematoxylin and washed in running water for 10 min.
(9) The tissue slices were dehydrated with an ethanol solution, and sealed with xylene. The stained slices were observed with a microscope and classified according to the following criteria. The stained sites (cytoplasm, cell membrane) were also confirmed. The results are shown in Table 2.

TABLE 2

| Antibody | Anti-GM2 antibody | | | | | | Human IgG1 | | |
|---|---|---|---|---|---|---|---|---|---|
| Tissue/ | 20 μg/mL | | | 2 μg/mL | | | 20 μg/mL | | |
| Xenograft cell | S | I | F | S | I | F | S | I | F |
| MSTO-211H | Tumor cell | C, M | 3+ | 4 | C, M | 3+ | 4 | Neg | | |
| | Other tissue | Neg | | | Neg | | | Neg | | |

Definitions of site and staining: M, cell membrane; C, cytoplasm
Criteria of staining intensity: Neg, negative; 1+, faint; 2+, pale; 3+, medium; 4+, dark
Criteria of staining frequency: Neg, (non-labeled cells "negative"); 1: <25%, 2: >=25%, <50%, 3: >=50%, <75%, 4: >=75%
S: site; I: intensity; F: frequency As a result, staining of the cell membrane and the cytoplasm was confirmed in the tumor of human malignant mesothelioma cell line MSTO-211H orthotopically grafted into the mouse thoracic cavity, demonstrating GM2 expression in the cell membrane and the cytoplasm of the orthotopically grafted mesothelioma cells.

Example 5

GM2 Expression Analysis by Fluorescence Immunohistochemical Staining with Human Malignant Mesothelioma Frozen Tissue A human malignant mesothelioma frozen slice embedded in an OCT compound, or a human malignant mesothelioma frozen block was obtained from Origene, and used for fluorescence immunohistochemical staining. Donor information is shown in FIG. 4.

Further, for comparison, a tumor block was removed from the chest region of an SCID mouse orthotopically grafted with human malignant mesothelioma cell line MSTO-211H, and embedded in an OCT compound to prepare a frozen tissue block.

The frozen block was sliced, and used for staining according to the following procedures.
(1) The frozen slices were fixed in anhydrous acetone at room temperature for 5 min, and air dried for 30 min.
(2) The frozen slices were washed with PBS for 5 min.
(3) The frozen slice was allowed to react at room temperature for 20 min in 1 μg/mL DAPI prepared with ddH$_2$O.
(4) The frozen slices were washed with PBS for 5 min.
(5) The frozen slices were reacted in 5% FBS-PBS at room temperature for 10 min.
(6) The frozen slices were reacted at 4° C. for 6 hours in 30 μg/mL of a primary antibody (Alexa 488-labeled BIW-8962 or Alexa 488-labeled anti-DNP antibody) prepared with PBS.
(7) The frozen slices were washed three times with H$_2$O for 1 min.
(8) A cover glass was placed on the frozen slice, and the slice was observed with a fluorescence microscope, and classified according to the following criteria. The results are shown in Table 3.

In Table 3, staining intensity is scaled from 0 to 3.
0: No staining
1: Very weak staining
2: Clear staining
3: Strong staining

TABLE 3

| Sample | Frequency (%) | Staining intensity | Stroma staining | Histological type |
|---|---|---|---|---|
| FR0001D4BA | 0 | 0 | | B |
| FR00020029 | 30 | 2 | | B |
| FR0002081F | 0 | 0 | | Meso |
| FR000265FD | 0 | 0 | | Meso |
| FR0002731F | 30 | 3 | | Meso |
| FR00026B23 | 0 | 0 | | B |
| FR000265A2 | 0 | 0 | | B |
| FR0002939E | 80 | 2 | | B |
| FR00035469 | 30 | 1 | Strong | Meso |
| FR000011E5 | 0 | 0 | | Meso |
| FR00002E6B | 0 | 0 | Medium | Desmoplastic |
| FR00006328 | 50 | 3 | | Meso |
| FR00006A38 | 0 | 0 | | Meso |
| FR00018ABD | 100 | 2 | Strong | Desmoplastic |
| FR00016972 | 0 | 0 | | Desmoplastic |
| SX00002843 | 90 | 1 | Strong | E |
| FR00005932 | 10 | 1 | Strong | Meso |
| FR00004AF8 | 40 | 3 | Strong | B |
| FR00005E39 | 80 | 3 | | Desmoplastic |
| FR00017430 | 100 | 3 | | Meso |
| FR0001A6C1 | 100 | 1 | Strong | B + Desmoplastic |
| FR0001CA2A | 100 | 3 | | NR |
| FR0001742F | 50 | 3 | | Meso |
| FR000265FE | 20 | 2 | | Meso |
| FR000293A0 | 0 | 0 | | B |
| FR00002E64 | 0 | 0 | | E |
| Positive control MSTO-211H | 90 | 3 | | |

Note)
Histological type: B, biphasic; E epithelial; Meso, mesothelial tumor with no subtype; Desmoplastic, fibrous; NR, unreported As a result, GM2 expression in tumor cells was confirmed in 15 of the 26 samples in an intensity range of 1 to 3. The same or higher reactivity was confirmed in 7 samples (27%) compared to the tumor tissue slices originating from the human malignant mesothelioma cell line MSTO-211H orthotopic graft mouse used as positive control.

These results demonstrated high ganglioside GM2 expression in human clinical malignant mesothelioma.

Although the present invention has been described in connection with the specific embodiments, it will be apparent to those skilled in the art that various modifications and changes may be made thereto without departing from the scope and spirit of the present invention. This application is based on U.S. Provisional Application No. 61/734,087 filed Dec. 6, 2012, the entire contents of which are incorporated hereinto by reference
SEQ ID NO: 1: amino acid sequence of HCDR1
SEQ ID NO: 2: amino acid sequence of HCDR2
SEQ ID NO: 3: amino acid sequence of HCDR3
SEQ ID NO: 4: amino acid sequence of LCDR1
SEQ ID NO: 5: amino acid sequence of LCDR2
SEQ ID NO: 6: amino acid sequence of LCDR3
SEQ ID NO: 7: amino acid sequence of humanized VH
SEQ ID NO: 8: amino acid sequence of humanized VL
SEQ ID NO: 9: amino acid sequence of humanized VL
SEQ ID NO: 10: amino acid sequence of humanized VH
SEQ ID NO: 11: amino acid sequence of humanized VL

What is claimed is:

1. A method for treating mesothelioma, comprising administering as an active ingredient an antibody or a fragment thereof that binds to a ganglioside GM2 into a subject in need thereof,
wherein the antibody comprises heavy chain (H-chain) complementarity determining regions (CDRs) 1 to 3 having the amino acid sequences of SEQ ID NOS: 1 to 3, respectively, and light chain (L-chain) CDRs 1 to 3 having the amino acid sequences of SEQ ID NOS: 4 to 6, respectively.

2. The treating method according to claim 1, wherein the mesothelioma is one selected from the group consisting of pleural mesothelioma, peritoneal mesothelioma and pericardial mesothelioma.

3. The treating method according to claim 2, wherein the pleural mesothelioma or the peritoneal mesothelioma is malignant pleural mesothelioma or malignant peritoneal mesothelioma.

4. The treating method according to claim 1, wherein the antibody is an antibody that binds to the α2-3 linked sialic acid of GM2.

5. The treating method according to claim 1, wherein the antibody is a monoclonal antibody.

6. The treating method according to claim 1, wherein the antibody is a recombinant antibody.

7. The treating method according to claim 6, wherein the recombinant antibody is one selected from the group consisting of a chimeric antibody, a humanized antibody, and a human antibody.

8. A method for treating mesothelioma, comprising administering as an active ingredient an antibody or a fragment thereof that binds to a ganglioside GM2 into a subject in need thereof,
wherein the antibody is one selected from the group consisting of:
an antibody that comprises an H-chain variable region (VH) having the amino acid sequence of SEQ ID NO: 7 and an L-chain variable region (VL) having the amino acid sequence of SEQ ID NO: 8;
an antibody that comprises a VH having the amino acid sequence of SEQ ID NO: 7 and a VL having the amino acid sequence of SEQ ID NO: 9;
an antibody that comprises a VH having the amino acid sequence of SEQ ID NO: 10 and a VL having the amino acid sequence of SEQ ID NO: 8; and
an antibody that comprises a VH having the amino acid sequence of SEQ ID NO: 10 and a VL having the amino acid sequence of SEQ ID NO: 11.

9. The treating method according to claim 1, comprising administering at least one additional drug.

10. The treating method according to claim 9, wherein the additional drug is at least one selected from the group consisting of a chemotherapeutic agent and a protein drug.

11. A pharmaceutical composition comprising:
an antibody or a fragment thereof that binds to a ganglioside GM2; and
a pharmaceutically acceptable carrier,
wherein said antibody comprises heavy chain complementarity determining regions (CDRs) 1 to 3 having the amino acid sequences of SEQ ID NOS: 1 to 3, respectively, and light chain CDRs 1 to 3 having the amino acid sequences of SEQ ID NOS: 4 to 6, respectively.

12. A pharmaceutical composition comprising:
an antibody or a fragment thereof that binds to a ganglioside GM2; and
a pharmaceutically acceptable carrier,
said antibody is one selected from the group consisting of:
an antibody that comprises an H-chain variable region (VH) having the amino acid sequence of SEQ ID NO: 7 and an L-chain variable region (VL) having the amino acid sequence of SEQ ID NO: 8;
an antibody that comprises a VH having the amino acid sequence of SEQ ID NO: 7 and a VL having the amino acid sequence of SEQ ID NO: 9;
an antibody that comprises a VH having the amino acid sequence of SEQ ID NO: 10 and a VL having the amino acid sequence of SEQ ID NO: 8; and
an antibody that comprises a VH having the amino acid sequence of SEQ ID NO: 10 and a VL having the amino acid sequence of SEQ ID NO: 11.

13. The composition of claim 11, which further comprises at least one additional drug.

14. The composition of claim 13, wherein the additional drug is at least one selected from the group consisting of a chemotherapeutic agent and a protein drug.

15. The composition of claim 12, which further comprises at least one additional drug.

16. The composition of claim 15, wherein the additional drug is at least one selected from the group consisting of a chemotherapeutic agent and a protein drug.

17. A method for diagnosing mesothelioma, comprising detecting or assaying a GM2, cell, or tissue in a sample by employing an antibody or a fragment thereof that binds to a ganglioside GM2,
wherein the antibody comprises heavy chain (H-chain) complementarity determining regions (CDRs) 1 to 3 having the amino acid sequences of SEQ ID NOS: 1 to 3, respectively, and light chain (L-chain) CDRs 1 to 3 having the amino acid sequences of SEQ ID NOS: 4 to 6, respectively; and
wherein the antibody is a recombinant antibody selected from the group consisting of a human chimeric antibody, humanized antibody, and human antibody.

18. The diagnosing method according to claim 17, wherein the mesothelioma is one selected from the group consisting of pleural mesothelioma, peritoneal mesothelioma and pericardial mesothelioma.

19. The diagnosing method according to claim 18, wherein the pleural mesothelioma or the peritoneal mesothelioma is malignant pleural mesothelioma or malignant peritoneal mesothelioma.

20. The diagnosing method according to claim 17, wherein the antibody is an antibody that binds to the α2-3 linked sialic acid of GM2.

21. The diagnosing method according to claim 17, wherein the antibody is a monoclonal antibody.

22. A method for diagnosing mesothelioma, comprising detecting or assaying a GM2, cell, or tissue in a sample by employing an antibody or a fragment thereof that binds to a ganglioside GM2, wherein the antibody is one selected from the group consisting of:
an antibody that comprises an H-chain variable region (VH) having the amino acid sequence of SEQ ID NO: 7 and an L-chain variable region (VL) having the amino acid sequence of SEQ ID NO: 8;
an antibody that comprises a VH having the amino acid sequence of SEQ ID NO: 7 and a VL having the amino acid sequence of SEQ ID NO: 9;
an antibody that comprises a VH having the amino acid sequence of SEQ ID NO: 10 and a VL having the amino acid sequence of SEQ ID NO: 8; and
an antibody that comprises a VH having the amino acid sequence of SEQ ID NO: 10 and a VL having the amino acid sequence of SEQ ID NO: 11.

* * * * *